United States Patent [19]

Manimaran et al.

[11] Patent Number: 5,015,764

[45] Date of Patent: May 14, 1991

[54] PREPARATION OF OPTICALLY ACTIVE ALIPHATIC CARBOXYLIC ACIDS

[75] Inventors: Thanikavelu Manimaran; Fred J. Impastato, both of Baton Rouge, La.

[73] Assignee: Ethyl Corporation, Richmond, Va.

[21] Appl. No.: 539,121

[22] Filed: Jun. 18, 1990

[51] Int. Cl.$^5$ .............................................. C07B 57/00
[52] U.S. Cl. ................................... 562/401; 548/572; 549/79; 549/499; 560/55; 560/56; 560/100; 560/102; 560/105; 560/265; 558/354; 562/466; 562/469; 562/490; 562/496; 562/606
[58] Field of Search ............... 562/401, 466, 469, 606, 562/496, 490; 558/354; 560/56, 55, 100, 102, 105, 265; 548/572; 549/79, 499

[56] References Cited

U.S. PATENT DOCUMENTS 4,786,731 11/1988 Russell ................................ 544/354

4,865,770 9/1989 Piscelli ................................ 562/402

*Primary Examiner*—Jose G. Dees
*Assistant Examiner*—Vera C. Clarke
*Attorney, Agent, or Firm*—Richard J. Hammond

[57] ABSTRACT

A process for the separation of a racemic mixture of certain aliphatic carboxylic acids or esters thereof is disclosed. The process comprises (i) forming a salt solution comprising said racemic mixture of a $C_1$ to $C_6$ linear or branched aliphatic carboxylic acid and an organic or inorganic base (ii) treating said salt solution with one-half molar equivalent of a chiral organic nitrogenous base having a base strength no stronger than said organic or inorganic base (iii) precipitating from the reaction solution formed in step (ii) the less soluble diastereomeric salt and (iv) separating said precipitated diastereomeric salt.

23 Claims, No Drawings

PREPARATION OF OPTICALLY ACTIVE ALIPHATIC CARBOXYLIC ACIDS

This invention relates to the preparation of optically active carboxylic acids and the esters thereof. More particularly this invention relates to the preparation of aliphatic carboxylic acids and the esters thereof by first forming the diasteromeric salts of such materials and then separating the diasteromeric salts.

It has been known that alcohols may be carboxylated to form carboxylic acids containing one or more carbon atoms than the starting material. In such carboxylations, either carbon monoxide or mixtures thereof with hydrogen have been used, the reaction conditions as to temperature and pressure as well as catalysts to effect the reaction being widely varied. See, for example, U.S. Pat. Nos. 2,805,248 and 4,356,953.

While the successful utilization of the above prior art reactions can result in the production of profen-type compounds (aryl substituted propionic acid and esters thereof), the most acceptable method for the commercial preparation of these compounds start with the corresponding ketone, i.e. 4-isobutylacetophenone for the preparation of 2-(4'-isobutylphenyl)propionic acid. Thus, for example, British Pat. No. 971,700 and corresponding U.S. Pat. No. 3,385,886, both assigned to Boots Company, show the production of phenylalkane derivatives in which the first step of the process is the reaction of a phenylalkane with acetyl chloride in the presence of aluminum chloride to produce an alkylphenylacetophenone which is then subjected to any of a series of subsequent reactions to produce the desired derivative.

Japanese Kokai Pat. No. SHO 55[1980]-27147, published Feb. 27, 1980 and assigned to Mitsubishi Petrochemical Co., discloses the formation of aryl substituted carboxylic acids, e.g., α(4'-isobutylphenyl)propionic acid by reacting an arylsubstituted alcohol, e.g., 1-(4'-isobutylphenyl)ethanol, with carbon monoxide and water in the presence of a hydrogen fluoride catalyst.

Japanese Kokai Pat. No. SHO 59[1984]-95238, published June 1, 1984 and assigned to Mitsubishi Petrochemical Co., teaches the formation of phenylacetic acid derivatives such as α-aryl-substituted propionic acids, where the aryl group may be a phenyl group containing at least one alkoxy, aryloxy, hydroxy, or amino group as an electron-donor substituent, by reacting a benzyl alcohol derivative, which may be an α-aryl substituted ethanol wherein the aryl group is the same as in the phenylacetic acid derivative product, with carbon monoxide and water, alcohol, or phenol, in the presence of a palladium catalyst. An acidic compound such as hydrogen chloride may be added as an auxillary catalyst and a solvent such as benzene may also be used. The disclosure includes a comparative example in which ibuprofen (not included within the invention) is obtained.

Japanese Kokai Pat. No. SHO 59[1984]-95239, published June 1, 1984 and assigned to Mitsubishi Petrochemical Co., discloses the formation of a α-(6-methoxy-2-naphthyl)propionic acid by reacting α-(6-methoxy-2-naphthyl)ethyl alcohol with carbon monoxide and water in the presence of a palladium catalyst and an acidic compound, e.g., hydrogen chloride. The patent publication also states that if a non-halogen-containing acidic compound is used, it is desirable to add an ionizable metal halide to the reaction.

Baddely, et al, Journal of the Chemical Society, 4943-4945 [1956], discloses on page 4945 the preparation of 4'-isobutylacetophenone by the Friedel-Crafts acetylation of isobutylbenzene with acetyl chloride using aluminum chloride as catalyst.

Japanese Patent Publication (Early Disclosure) No. 60 [1985]-188,643 discloses the preparation of p-isobutylacetophenone by the acetylation of isobutylbenzene using as an acetylating agent acetyl fluoride prepared by reacting acetic anhydride with hydrogen fluoride, and as a catalyst, a combination of hydrogen fluoride and boron trifluoride.

Japanese Kokuku Pat. No. SHO 56 [1981]-35659, published Sept. 4, 1978 discloses an anhydrous method of producing a 2-(4'-isobutylphenyl)propionic acid ester by treating 1-(4'-isobutylphenyl)ethanol with carbon monoxide in a solution containing an alkanol and a catalyst such as palladium bis(triphenylphosphine) dichloro complex. The solution may also contain up to 10% of a mineral acid such as hydrogen chloride.

Resolution of racemic aryl-substituted aliphatic carboxylic acids has been described in the literature. Kaiser et al, J. Pharm. Sci., Vol. 65, No. 2, 269-273 (February 1976) formed the S(−)α-methylbenzylamine salt of S(+) ibuprofen removed it from the reaction mixture by filtration and recrystallized it from isopropanol and then from methanol. After acidifying with 3N aqueous sulfuric acid, and extracting with ether, S(+)-ibuprofen was obtained, m.p. 50·14 52·,$[\alpha]_D$+57·with 95% optical purity as determined by GLC analysis. Cox et al, J. Pharmacol Exp Ther, Vol. 232, No. 3, 636-643 (March 1985), using Kaiser et al's method, were able to obtain an S(+)-ibuprofen preparation which was 99% S isomer and 1% R isomer (w/w).

Other methods of separating the enantiomers of racemates can be effected by preparing a salt of the acid with an alkaloid or similar resolving agent such as cinchonidine, then separating the products by fractional crystallization from a solvent in which the salt of the dextrorotatory isomer is least soluble. The (+)-salt can then be acid cleaved to yield pure enantiomer. See for example U.S. Pat. No. 4,209,638 issued June 24, 1980, Alvarez U.S. Pat. No. 3,637,767 issued Jan. 25, 1972, which relates to resolution of naproxen and related compounds.

According to the present invention, there is provided a process for increasing the amount of the desired enantiomer obtained from a racemic mixture of $C_1$ to $C_6$ linear or branched aliphatic carboxylic acid or ester thereof. The process comprises (i) forming a salt solution comprising the racemic mixture of the $C_1$ to $C_6$ linear or branched aliphatic carboxylic acid or ester thereof and an organic or inorganic base (ii) treating said salt solution with a chiral organic nitrogenous base having a base strength no stronger than said organic base, inorganic base or mixtures of an organic base and an inorganic base (iii) precipitating from the reaction solution produced in the treatment of step (ii) the less soluble diastereomeric salt and (iv) separating said diastereomeric salt.

The $C_1$ to $C_6$ linear or branched aliphatic carboxylic acids and esters useful in the process of the present invention have the formula

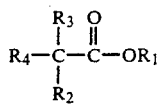

where $R_1$ is hydrogen or $C_1$ to $C_6$ linear or branched alkyl, $R_2$, $R_3$ and $R_4$ are different and are hydrogen or $C_1$ to $C_6$ linear or branched alkyl, e.g. methyl or ethyl; aralkyl, e.g., benzyl; cycloalkyl, e.g. cyclopropyl, cyclobutyl, cyclopentyl, cyclohexyl; alkyl substituted cycloalkyl e.g. methylcyclohexyl; $C_6$ to $C_{10}$ aryl, e.g. phenyl unsubstituted or substituted with for example methyl, dimethyl, butyl especially isobutyl or phenyl substituted with $C_1$ to $C_4$ alkylthio, $C_1$ to $C_4$ alkoxy, cyano or halo e.g. fluoro or chloro; $C_1$ to $C_6$ linear or branched alkoxy, e.g. phenoxy or phenoxy substituted with for example methyl, dimethyl, butyl or isobutyl or phenoxy substituted with $C_1$ to $C_4$ alkylthio, $C_1$ to $C_4$ alkoxy, cyano or halo; $C_1$ to $C_6$ alkylthio, e.g. methylthio; $C_2$ to $C_8$ cycloalkylthio; $C_6$ to $C_{10}$ arylthio; $C_6$ to $C_{10}$ arylcarbonyl e.g. benzoyl; $C_4$ to $C_8$ cycloalkenyl e.g. cyclohexenyl; trifluoromethyl; halo e.g. fluoro or chloro; $C_4$ to $C_5$ heteroaryl e.g. furyl, pyrrolyl, thienyl; or $C_{10}$ to $C_{14}$ aryl e.g..naphthyl or naphtyl substituted with $C_1$ to $C_4$ alkyl e.g. methyl; $C_1$ to $C_4$ alkoxy, e.g. ethoxy, halo; or biphenyl unsubstituted or substituted with methyl or halo, especially fluoro.

Preferred compounds of formula I are those of the formula

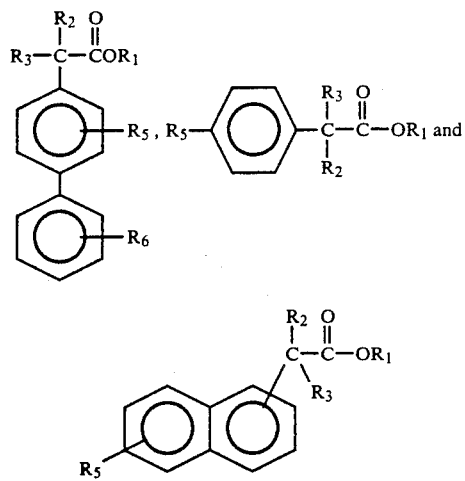

where $R_1$, $R_2$ and $R_3$ are as previously defined and $R_5$ and $R_6$ are $C_1$ to $C_4$ linear or branched alkyl, $C_1$ to $C_4$ linear or branched alkoxy or halo.

The process of the present invention is particularly applicable to 2-(4-isobutylphenyl)propionic acid and especially in obtaining a preponderance of the S(+) isomer.

The invention is carried out by using a racemic mixture (a mixture of both the (+) and (−) or dextro and levo rotatory forms) or a mixture containing a preponderance of one of the enantiomers of these carboxylic acids. The use of racemic mixtures is preferred. However it should be understood that in this step, the process itself does not convert one form of the stereoisomers to the other form but only separates such forms. Further because the separation of isomers gives rise to a soluble product largely containing one enantiomer and an insoluble product largely containing the other enantiomer, a high purity salt is obtained that requires a minimum number of recrystallizations (usually not more than two) to give a product with exceptional high optical purity.

The purified salt obtained from the process of the present invention may be further treated to produce the free aliphatic carboxylic acid thereof by using any conventional means. For example, hydroylsis of the salt with a dilute mineral acid and extraction with a suitable organic solvent produces the purified aliphatic carboxylic acid. Further extraction and recrystallization with a suitable solvent can increase the purity to even a greater extent.

The first step in the reaction sequence for the separation of the racemic mixtures used in the present invention is to form a salt solution of the aliphatic carboxylic acid with an organic or inorganic base. When such base is an inorganic one, it is preferred that it is a metallic or ammonium hydroxide, carbonate or bicarbonate, the metal being from Group IA or IIA of the Periodic Table of Elements. Most preferably, the inorganic base is potassium hydroxide. Advantageously, when the base used is an inorganic one, the solvent useful for carrying out this phase of the separation process is water.

When the base used in the first step of the separation process is an organic base then it is preferably an aliphatic, aromatic or mixed aliphatic and aromatic amine. The only criteria for such organic base is that it take part in no other reaction with the aliphatic carboxylic acid except salt formation, that it be soluble in the solution first used in the process of the present invention and that it have a base strength equivalent to or greater than the base strength of the chiral, organic nitrogenous base used in the subsequent step of the reaction (the same criteria are true for the inorganic base as well). Preferred organic bases are the tri substituted $C_1$ to $C_6$ linear or branched alkyl amines and the tri substituted mixed $C_1$ to $C_6$ linear or branched alkyl, $C_6$ to $C_{10}$ arylamines such as triethylamine, phenyl diethylamine and the like. Where such organic base is used in this first step, then the solvent employed to form the salt solution is preferably a liquid, inert, organic one. Most preferably such solvents include the aliphatic hydrocarbon solvents, i.e. $C_4$ to $C_{14}$ hydrocarbons. Particularly preferred is hexane or octane as such solvent.

At this point in the reaction sequence (during the admixture of the base and the aliphatic carboxylic acid or ester) the salt solution may be heated e.g. to a temperature of about 25° C. to about 125° C., preferably about 75° C. to 120° C. or the heating can occur after the salt solution is formed and before the chiral organic nitrogenous base is added. Heating can also be carried out after the chiral organic nitrogenous base is added. Heating is typically carried out from about 1 to about 16 hours. Preferably from about 2 to about 8 hours.

As noted for the requirements for the inorganic and the organic base, the chiral organic nitrogenous base must have a base strength equal to or at least not significantly greater than that of the inorganic or organic base. Surprisingly, the chiral organic nitrogenous base forms a more stable salt with the isomers of the aliphatic carboxylic acid displacing the inorganic or organic base. Additionally because of the presence of the inorganic or organic base, one of the diastereomeric salts formed from the subsequent displacement of the inorganic or organic base by the chiral organic nitrogenous base is more soluble in the reaction solution (the solution formed when the chiral base is added to the salt solution), the other of course precipitates. The solid precipitated is readily separated from the solution by conventional techniques, i.e. centrifugation, filtration and the like.

Generally the chiral organic nitrogenous base is a $C_1$ to $C_6$ linear or branched aliphatic amine unsubstituted or substituted with $C_6$ to $C_{10}$ aryl group that is unsubstituted or substituted with $C_1$ to $C_6$ alkyl, $C_1$ to $C_6$ alkoxy, $C_1$ to $C_6$ alkoxy or halo. Preferably such chiral organic nitrogenous base is an α-monosubstituted alkylamine, and preferably an α-monosubstituted ethylamine, especially an α-phenylethylamine in which the phenyl ring may be substituted by one or more groups such as alkyl e.g. $C_{1-4}$ alkyl, especially isopropyl, halogen, e.g. chlorine or fluorine, alkoxy e.g. $C_{1-4}$, especially methoxy. Particularly preferred bases are (−)-α-methylbenzylamine and (−)-α-(2-methoxyphenyl) ethylamine. Other suitable bases include (−)-α-(3-chlorophenyl)ethylamine, (−)-α-(4-fluorophenyl)ethylamine, (−)-α-(2-fluorophenyl)ethylamine, (−)-α-(2chlorophenyl)ethylamine, (+)-α-(2-methoxyphenyl)ethylamine, (−)-α-(2,6-dimethoxyphenyl)ethylamine and also (+)-α-cyclohexylethylamine.

It should be noted that the process of the present invention is particularly adapted to the economical conversion of racemic mixtures to the diasteromeric S- or (+)- component. (Of course, the R-component may be the least soluble one, in which case the following discussion should be applied in reverse). The method of the present invention essentially provides a solid precipitate enriched in the S-enantiomer and a liquid filtrate enriched in the R- or (−)- enantiomer. Liberation of the desired S-enantiomer from the precipitated salt is readily accomplished by acidification of the salt with for example dilute mineral acid or any other inorganic or organic acid conventionally known to hydrolyze salts of this nature. While this procedure leaves the filtrate as an undesired by product, it can be further treated with acid or base to convert the R-enriched filtrate to the racemic mixture. This mixture can then be reused in the process of the present invention, using the chiral organic base recovered from the above conversion step. Thus, the process of the present invention lends itself readily to a recycling-type of procedure.

The invention is illustrated by the following Examples.

EXAMPLE 1

Resolution of Ibuprofen with α-Methylbenzylamine and Triethylamine in Octane

A 300 mL flask equipped with a magnetic stir bar was charged with racemic ibuprofen (10.3 g; 50 mmol) and triethylamine (5.1 g; 51 mmol) in 10 mL of octane. The solution was stirred and heated to 125° C. To the hot solution, 3 g (25 mmol) of S-(−)-α-methylbenzylamine (MBA) was added in drops. After the addition, the hot clear solution was stirred for 3 hours and then allowed to cool to room temperature. The white solid precipitated on cooling was isolated by filtration to obtain quantitative yield (8.1 g; 25 mmol) of the MBA salt of ibuprofen. Ibuprofen liberated from this salt had a specific rotation of +36.6°. The salt was recrystallized twice in 80 mL of 2-propanol to get 5.6 g (69% yield) of pure MBA salt; m.p. 173°–175° C.

The pure salt was added to 50 mL of 5% aqueous hydrochloric acid and stirred. After 30 minutes, the product was filtered, washed with water and dried to give 3.4 g of 99% pure S-ibuprofen; m.p. 48°–40° C.; $[\alpha]_D = +56°$.

EXAMPLE 2

Resolution of Ibuprofen with α-Methylbenzylamine and Potassium Hydroxide in Water A flask was charged with racemic ibuprofen (10.3 g; 50 mmol), potassium hydroxide (1.4 g; 25 mmol) and 100 mL of water and heated to 80° C. 3 g (25 mmol) of (−)-α-methylbenzylamine was added slowly to the hot solution while stirring. A few minutes after the addition, the MBA salt began to precipitate. The mixture was heated at 80° C. for 2 hours. It was then allowed to cool to room temperature and filtered. The white solid was dried to give 7.92 g of the MBA salt. Ibuprofen liberated from a small amount of this salt had a specific rotation of +35°.

EXAMPLE 3

Resolution of Ibuprofen with α-Methylbenzvlamine and Triethylamine in Water

A flask was charged with a salt solution of ibuprofen 10.3 g; 50 mmol) and triethylamine (5.1 g; 51 mmol) in 100 mL of water and heated to 95° C. To the hot solution, (−)-α-methylbenzylamine (3 g; 25 mmol) was added in drops with stirring. When a white solid started precipitating, the reaction mixture was cooled to room temperature. The precipitate was isolated by filtration and dried to give 8 g of the MBA salt. Ibuprofen liberated from this salt had a specific rotation of +35°.

EXAMPLE 4

Resolution of Ibuorofen with α-Methylbenzylamine in Water (Without any additional achiral base)

A flask was charged with racemic ibuprofen (10.3 g; 50 mmol) and water (80 mL) and the mixture was heated to 55° C. (−)-α-Methylbenzylamine (3 g; 25 mmol) was slowly added. The MBA salt began to precipitate and the mixture was stirred at 55° C. for 4 hours. Then it was filtered hot to isolate 7.6 g of the MBA salt. The specific rotation of ibuprofen liberated from this salt was +29°.

EXAMPLE 5

Resolution with (−)MBA, Potassium Hydroxide and Triethanolamine

Racemic ibuprofen (10.3 g; 50 mmol) was dissolved in a mixture of 1.4 g (25 mmol) of potassium hydroxide and 3.75 g (25 mmol) of triethanolamine in 100 mL of water and heated to 85° C. To the hot solution, 3 g (25 mmol) of (−)-MBA was slowly added; a few minutes after the addition, a white solid precipitated. The mixture was stirred at 85° C. for 64 hours and then cooled to room temperature. The white precipitate was isolated by filtration and dried to give 7.9 g of the MBA salt. Ibuprofen liberated from this salt had $[\alpha]_D = +33°$.

EXAMPLE 6

Resolution with (−) MBA and Triethvlamine at Room Temperature

A 250 mL Erlenmeyer flask equipped with a magnetic stir bar was charged with a salt solution of 10.3 g (50 mmol) of racemic ibuprofen and 10 mL (70 mmol) of triethylamine in 100 mL of water. 3 g (25 mmol) of (−)MBA was added to this solution and stirred overnight (16 hours) at room temperature. The precipitated white solid was isolated by filtration and dried to obtain 8 g of the MBA salt; the specific rotation of ibuprofen obtained from this salt was +32°.

EXAMPLE 7

Resolution with (−)MBA and Ammonium Hydroxide

A solution of ammonium salt of ibuprofen was obtained by stirring 10.3 g (50 mmol) of racemic ibuprofen with 25 mL of concentrated ammonium hydroxide solution and 100 mL of water. The solution was stirred and heated to 65° 3 g (25 mmol) of (−)MBA was added slowly. The thick precipitate obtained was stirred overnight (16 hours) at 65° C. After cooling to about 45° C., the precipitate was filtered and dried. The yield of MBA salt was 7.8 g and the rotation of ibuprofen from this salt was +35°.

EXAMPLE 8

Racemization of unwanted R-ibuorofen from the filtrate

Ibuprofen was isolated from the filtrate obtained after separation of the MBA salt was found to be enriched with the R-isomer. It has a rotation of −25° to −28°. The following experiments demonstrate that it could be racemized for recycling.

(a) Racemization with Sodium Hydroxide in 2-Propanol

R-Ibuprofen (1.03 g; 5 mmol; $[\alpha]_D = -26°$) was dissolved in a solution of sodium hydrozide (0.8 g; 10 mmol) in 10 mL of 2-propanol and refluxed for 15 hours, Ibuprofen liberated from this mixture had $[\alpha]_D = 0°$, indicating that it was completely racemized.

(b) Racemization of R-Ibuorofen by treatment with Acid 500 mg of ibuprofen with $[\alpha]_D = -26°$ was taken in 5 mL of water and 2 mL of concentrated HCl. The suspension was refluxed for 72 hours. The mixture was then cooled, extracted with ether (30 mL) and solvent stripped to give 382 mg of racemic ibuprofen ($[\alpha]_D = 0°$).

(c) Racemization with Triethylamine in Octane 500 mg (2.5 mmol) of R-ibuprofen was dissolved in a solution of triethylamine (500 mg; 5 mmol) in 5 mL of octane and refluxed overnight (15 hours). After stripping the solvent, the residue was analyzed by a chiral column HPLC method and found to be racemic.

We claim:

1. A process for separating a racemic mixture of an aliphatic carboxylic acid or ester thereof having the formula

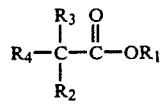

where $R_1$ is hydrogen or $C_1$ to $C_6$ linear or branched alkyl; $R_2$, $R_3$ and $R_4$ are different and are hydrogen or $C_1$ or $C_6$ linear or branched alkyl; cycloalkyl; alkyl-substituted cycloalkyl; $C_6$ to $C_{14}$ aryl; $C_1$ to $C_6$ linear or branched alkoxy; $C_1$ to $C_6$ alkylthio; $C_2$ to $C_8$ cycloalkylthio; $C_6$ to $C_{10}$ arylthio; $C_6$ to $C_{10}$ arylcarbonyl; $C_4$ to $C_8$ cycloalkenyl; trifluoromethyl; halo; or $C_4$ to $C_5$ heteroaryl; which comprises (i) forming a salt solution comprising said racemic mixture of an aliphatic carbox- ylic acid or ester thereof with an organic or inorganic base, (ii) treating said salt solution with a chiral organic nitrogenous base having a base strength no stronger than said organic or inorganic base, (iii) precipitating from the reaction solution formed in step (ii) the less soluble diastereomeric salt, and (iv) separating said precipitated diastereomeric salt.

2. The process according to claim 1 wherein said aliphatic carboxylic acid thereof is a 2-arylpropionic acid derivative thereof.

3. The process according to claim 2 wherein said ester is a $C_1$ to $C_6$ linear or branched ester.

4. The process of claim 1 wherein said solvent for said salt solution formed in step (i) is water and said base is an inorganic base.

5. The process according to claim 4 wherein said inorganic base is a metallic hydroxide, carbonate or bicarbonate, said metal being from Group IA or IIA of the Periodic Table of Elements.

6. The process according to claim 5 wherein said metal salt is potassium hydroxide.

7. The process of claim 1 wherein said chiral organic nitrogenous base is an $C_1$ to $C_6$ linear or branched aliphatic amine or a $C_1$ to $C_6$ linear or branched aliphatic amine further substituted with $C_6$ to $C_{10}$ aryl group that is unsubstituted or substituted with $C_1$ to $C_6$ alkyl, $C_1$ to $C_6$ alkoxy or halo, or $C_1$ to $C_6$ linear or branched alkoxy.

8. The process according to claim 5 wherein said chiral organic nitrogenous base is an α-monosubstituted alkylamine.

9. The process according to claim 6 wherein said chiral organic nitrogenous base is (−) alpha-methylbenzylamine.

10. The process of claim 7 wherein the solvent for said salt solution formed in step i) is a liquid inert organic solvent.

11. The process of claim 10 wherein said salt solution is anhydrous.

12. The process of claim 11 wherein said salt solution is treated with the chiral organic nitrogenous base at a temperature of from about 25° C. to about 125° C.

13. The process according to claim 12 wherein said treatment is carried out over a period of from about 1 hour to about 16 hours.

14. The process according to claim 13 wherein said aliphatic carboxylic acid is 2-(6-methoxy-2naphthyl)-propionic acid, 2-(4-isobutylphenyl)propionic acid or 2-(2-fluoro-4-biphenyl)propionic acid.

15. The process of claim 14 wherein said aliphatic carboxylic acid is 2-(4-isobutylphenyl) propionic acid.

16. The process of claim 14 wherein the mole ratios of the aliphatic carboxylic acid to the chiral organic nitrogenous base is from about 1 to 0.1 to about 0.1 to 1.

17. The process of claim 15 wherein the reaction solution has dissolved in it from about 50% to about 100% of the corresponding more soluble salt.

18. The process of claim 16 wherin the mole ratios of the aliphatic carboxylic acid to the chiral organic nitrogenous base is from about 1 to 0.5 to about 1 to 1.

19. A process according to claim 1 wherein said of an aliphatic carboxylic acid or ester thereof has the formula

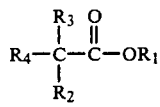

wherein $R_1$ is hydrogen or $C_1$ to $C_6$ linear or branched alkyl; $R_2$, $R_3$ and $R_4$ are methyl or ethyl, benzyl, cycloprophyl, cyclobutyl, cyclopentyl, cyclohexyl, methylcyclohexyl, phenyl unsubstituted or substituted with methyl, dimethyl butyl, isobutyl or phenyl substituted with $C_1$ to $C_4$ alkylthio, $C_1$ to $C_4$ alkoxy, cyano or fluoro or chloro, phenoxy or phenoxy substituted with methyl, dimethyl, butyl or isobutyl or phenoxy substituted with $C_1$ to $C_4$ alkylthio, $C_1$ to $C_4$ alkoxy, cyano or halo, methylthio; benzoyl, cyclohexenyl, trifluoromethyl, fluoro, chloro, benzyl, pyrrolyl, thienyl, naphthyl or naphthyl substituted with methyl, ethoxy or biphenyl unsubstituted or substituted with methyl or fluoro.

20. A process for separating the diasteriomers from a racemic mixture of 2-(4-isobutylphenyl)propionic acid which comprises (i) forming a salt solution comprising said racemic mixture and an organic base; (ii) treating said salt solution at a temperature of about 25° C. to about 125° C. with a chiral organic base $C_1$ to $C_6$ linear or branched aliphatic amine or a $C_1$ to $C_6$ linear or branched aliphatic amine further substituted with $C_6$ to $C_{10}$ aryl group that is unsubstituted or substituted with $C_1$ to $C_6$ alkyl, $C_1$ to $C_6$ alkoxy or halo, or $C_1$ to $C_6$ linear or branched alkoxy; (iii) precipitating from the reaction solution formed in step (ii) the less soluble diasteriomeric salt and (iv) separating said precipitated salt.

21. The process of claim 20 wherein said separated salt is hydrolyzed and the free optically active 2-(4-isobutylphenyl)propionic acid and the chiral amine are recovered.

22. The process of claim 21 wherein said optically active 2-(4-isobutylphenyl)propionic acid has S(+) configuration.

23. The process of claim 20 wherein a residual solution is obtained after separation of the precipitated salt containing the more soluble salt of R-enantiomer and said residual solution is treated to racemize said salt of R-enantiomer into the salt of racemic (R,S) mixture for recycling.

* * * * *